United States Patent
Biedermann et al.

(10) Patent No.: US 9,492,286 B2
(45) Date of Patent: Nov. 15, 2016

(54) INTERVERTEBRAL IMPLANT

(75) Inventors: Lutz Biedermann, VS-Villingen (DE); Wilfried Matthis, Weisweil (DE); Othmar Schwarzenbach, Steffisburg (CH)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/494,871

(22) Filed: Jun. 12, 2012

(65) Prior Publication Data

US 2013/0023937 A1 Jan. 24, 2013

Related U.S. Application Data

(60) Provisional application No. 61/496,801, filed on Jun. 14, 2011.

(30) Foreign Application Priority Data

Jun. 14, 2011 (EP) .................................. 11169884

(51) Int. Cl.
*A61B 17/88* (2006.01)
*A61F 2/44* (2006.01)
(Continued)

(52) U.S. Cl.
CPC ............ *A61F 2/4465* (2013.01); *A61F 2/4611* (2013.01); *A61F 2002/2835* (2013.01); *A61F 2002/305* (2013.01); *A61F 2002/30505* (2013.01); *A61F 2002/30538* (2013.01); *A61F 2002/30594* (2013.01); *A61F 2002/30596* (2013.01); *A61F 2002/30777* (2013.01); *A61F 2002/30784* (2013.01); *A61F 2002/30789* (2013.01); *A61F 2002/30841* (2013.01);
(Continued)

(58) Field of Classification Search
CPC ....................... A61F 2/4455; A61F 2002/4475
USPC ............................................. 623/17.11–17.16
See application file for complete search history.

(56) References Cited

U.S. PATENT DOCUMENTS 6,059,829 A * 5/2000 Schlapfer et al. .......... 623/17.16
6,319,257 B1 * 11/2001 Carignan et al. ............... 606/99
(Continued)

FOREIGN PATENT DOCUMENTS

DE 102008045174 A1 3/2010
WO WO 03/026538 A1 4/2003

OTHER PUBLICATIONS

Extended European Search Report for European Application No. 11169884.1, extended European Search Report dated Nov. 24, 2011 and mailed Dec. 2, 2011 (5 pgs.).

*Primary Examiner* — Jacqueline Johanas
(74) *Attorney, Agent, or Firm* — Lewis Roca Rothgerber Christie LLP (57) ABSTRACT

An intervertebral implant includes a first surface configured to engage a first vertebral body, a second surface configured to engage a second vertebral body, a side wall connecting the first surface and the second surface to define a hollow space of the implant, and a rotatable insert configured to be positioned in the space, wherein an elongate opening extends through the side wall into the space, and wherein the insert comprises a spring portion configured to hold the insert in the space by frictional engagement with the side wall and an engagement portion configured to engage with a tool through the opening when the insert is positioned in the space.

23 Claims, 8 Drawing Sheets

(51) Int. Cl.
*A61F 2/46* (2006.01)
*A61F 2/28* (2006.01)
*A61F 2/30* (2006.01)

(52) U.S. Cl.
CPC *A61F 2002/30843* (2013.01); *A61F 2002/448* (2013.01); *A61F 2002/4475* (2013.01); *A61F 2002/4623* (2013.01); *A61F 2002/4624* (2013.01); *A61F 2220/0025* (2013.01); *A61F 2250/0006* (2013.01); *A61F 2310/00023* (2013.01); *Y10T 29/49826* (2015.01)

(56) References Cited

U.S. PATENT DOCUMENTS

| | | | |
|---|---|---|---|
| 7,641,690 B2* | 1/2010 | Abdou | 623/17.11 |
| 7,935,148 B2 | 5/2011 | Edie et al. | |
| 8,753,400 B2* | 6/2014 | Ciupik | A61F 2/4465 623/17.11 |
| 2005/0038431 A1* | 2/2005 | Bartish et al. | 606/61 |
| 2005/0096745 A1* | 5/2005 | Andre et al. | 623/17.11 |
| 2005/0119747 A1* | 6/2005 | Fabris Monterumici et al. | 623/17.11 |
| 2007/0162129 A1 | 7/2007 | Edie et al. | |
| 2007/0213826 A1* | 9/2007 | Smith et al. | 623/17.11 |
| 2007/0282444 A1* | 12/2007 | Lo et al. | 623/17.11 |
| 2008/0009880 A1* | 1/2008 | Warnick et al. | 606/99 |
| 2008/0027544 A1 | 1/2008 | Melkent | |
| 2008/0091211 A1* | 4/2008 | Gately | 606/99 |
| 2008/0140085 A1 | 6/2008 | Gately et al. | |
| 2008/0147193 A1* | 6/2008 | Matthis et al. | 623/17.16 |
| 2008/0172128 A1* | 7/2008 | Perez-Cruet et al. | 623/17.16 |
| 2008/0221694 A1* | 9/2008 | Warnick et al. | 623/17.16 |
| 2010/0094422 A1* | 4/2010 | Hansell et al. | 623/17.16 |
| 2010/0114105 A1 | 5/2010 | Butters et al. | |
| 2010/0204798 A1* | 8/2010 | Gerbec et al. | 623/17.16 |
| 2010/0256759 A1 | 10/2010 | Hansell et al. | |
| 2010/0256760 A1 | 10/2010 | Hansell | |
| 2011/0009972 A1* | 1/2011 | Chauvin et al. | 623/17.16 |
| 2011/0276142 A1* | 11/2011 | Niemiec et al. | 623/17.16 |
| 2014/0052249 A1* | 2/2014 | Metz-Stavenhagen | 623/17.11 |

* cited by examiner

INTERVERTEBRAL IMPLANT

CROSS-REFERENCE TO RELATED APPLICATION(S)

The present application claims priority to and the benefit of U.S. Provisional Patent Application Ser. No. 61/496,801, filed Jun. 14, 2011, the contents of which are hereby incorporated by reference in their entirety, and claims priority from European Patent Application EP 11 169 884.1, filed Jun. 14, 2011, the contents of which are hereby incorporated by reference in their entirety.

BACKGROUND

Field of the Invention

The invention relates to an intervertebral implant that has a top surface configured to engage a first vertebral body, a bottom surface configured to engage a second vertebral body, and a side wall connecting the top surface and the bottom surface, a hollow space defined by the side wall and an elongate opening extending through the side wall into the space. The implant further includes a rotatable insert that is held within the space by a spring force. The insert has an engagement portion configured to engage with a tool through the opening.

Description of Related Art

An intervertebral implant configured to engage with an insertion device for inserting between first and second vertebral members is known from U.S. Pat. No. 7,935,148. The intervertebral implant has an opening including an elongated shape that extends through the side wall. A connection member including a receptacle is contained within the side wall. The insertion device has a first end configured to connect with the connection member of the implant body. The first end is selectively positionable between orientations to provide for the connection.

Another intervertebral implant is known from US 2010/0094422 A1. The implant has a support body and a rotatable insert therein. An installation instrument is also disclosed for removable attachment to the implant and engagement with the rotatable insert to selectively permit rotation between the insert and the support body.

SUMMARY

It is an object of the invention to provide an intervertebral implant that is simplified in terms of design and use, in view of the possibilities that are available for final positioning of the implant between vertebral bodies.

The intervertebral implant according to embodiments of the invention has a compact design. An insertion procedure of the implant is simple and safe, since a connection between the implant and an insertion tool can be easily fixed/tightened and loosened. When the connection between the tool and the implant is loosened, the implant can be moved into a desired position by rotating it relative to the tool. To this effect, the implant may include an insert that remains fixed relative to the tool, and the other portions of the implant may rotate relative to the insert. During rotation, the intervertebral implant is safely held by the insertion device and is prevented from inadvertent disconnecting from the tool.

The design of the intervertebral implant allows for a large portion of the hollow interior space of the implant to be available for fusion.

In some embodiments, existing intervertebral implants could be modified and upgraded with the insert.

BRIEF DESCRIPTION OF THE DRAWINGS

Further features and advantages of the invention will become apparent from the description of the accompanying drawings. In the drawings.

DETAILED DESCRIPTION

Figure 1:
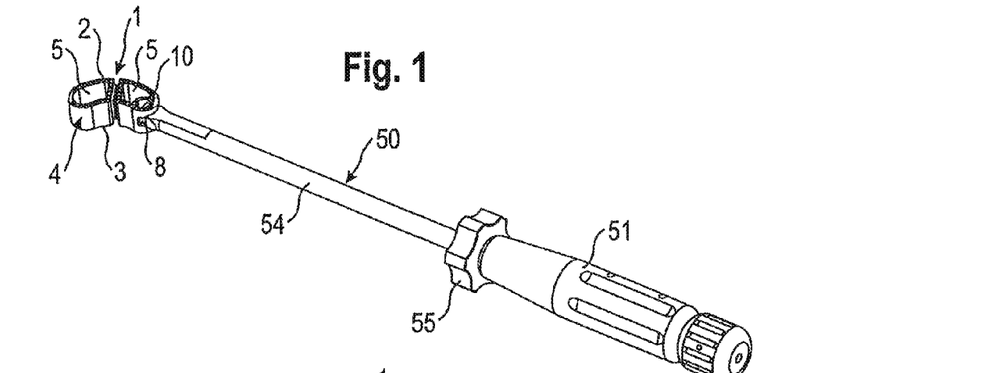
FIG. 1 shows a perspective view of an embodiment of an intervertebral implant and a tool for inserting the intervertebral implant.

FIG. 1 shows a perspective view of a first embodiment of an intervertebral implant 1 and a tool 50 for inserting the intervertebral implant 1. As shown in particular in FIGS. 1 to 3, the intervertebral implant 1 includes a top face 2, a bottom face 3, and a side wall 4 connecting the top face 2 and the bottom face 3. The side wall 4 defines an interior hollow section 5. The top face 2 and the bottom face 3 have openings so that the hollow interior section 5 extends into the top face 2 and the bottom face 3. Hence, the top face 2 and the bottom face 3 are formed by upper and lower rims of the side wall 4, respectively. Furthermore, a center wall 6 may be provided that separates the hollow interior section 5 in two parts. The height of the side wall 4 is such that the implant can be inserted between a first and a second vertebral body. The height of the implant 1 may be largest around the center wall 6 and may decrease towards outer ends of the implant 1. Teeth 7 or other engagement portions project from the top face 2 and the bottom face 3 for engaging end plates of the vertebral bodies.

The implant 1 has two opposite long sides 4a and two opposite short sides 4b connecting the long sides 4a. The short sides 4b are rounded. The contour of the side wall 4 may be arcuate, for example, it may have a kidney-shape or a banana-shape.

Figure 2:
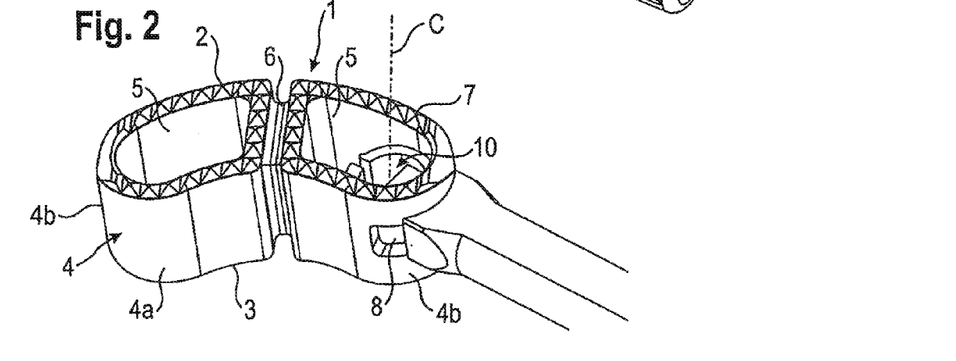
FIG. 2 shows an enlarged view of a portion of FIG. 1.
Figure 3:
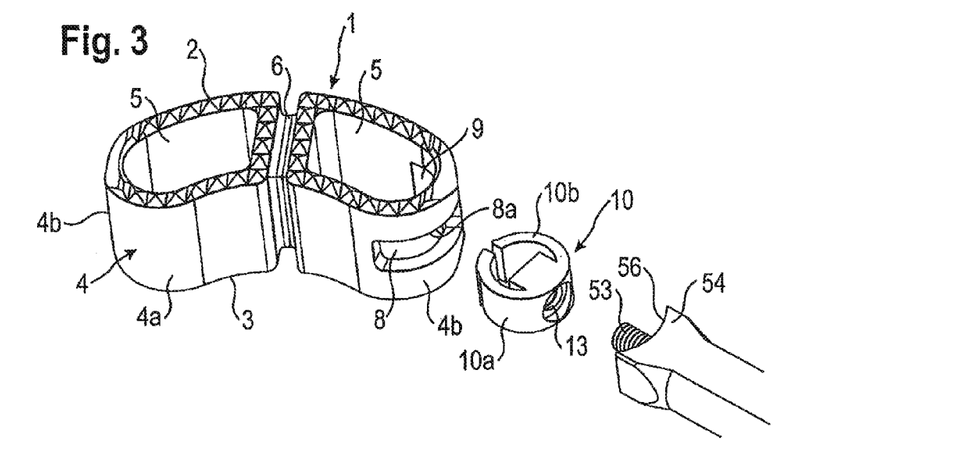
FIG. 3 shows an exploded perspective view of the enlarged portion in FIG. 2.
Figure 4:
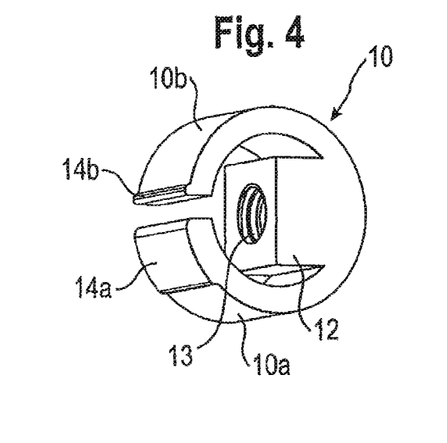
FIG. 4 shows a perspective view of an insert provided for an intervertebral implant according to an embodiment of the invention.
Figure 5:
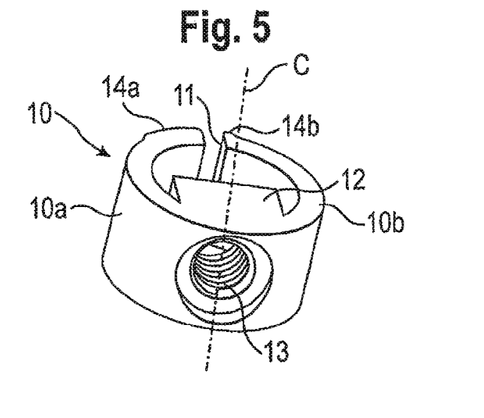
FIG. 5 shows another perspective view of the insert of FIG. 4.

As can be seen in particular in FIGS. 2 and 3, an opening 8 is provided in the side wall 4 that extends completely through the side wall 4 into the interior hollow section 5. The opening 8 has an elongate shape and extends preferably over a length in a circumferential direction along a short side 4b. The opening 8 may have a substantially rectangular contour and may be located substantially in a center of the side wall 4 along a vertical direction between the top face 2 and the bottom face 3.

Figure 6:
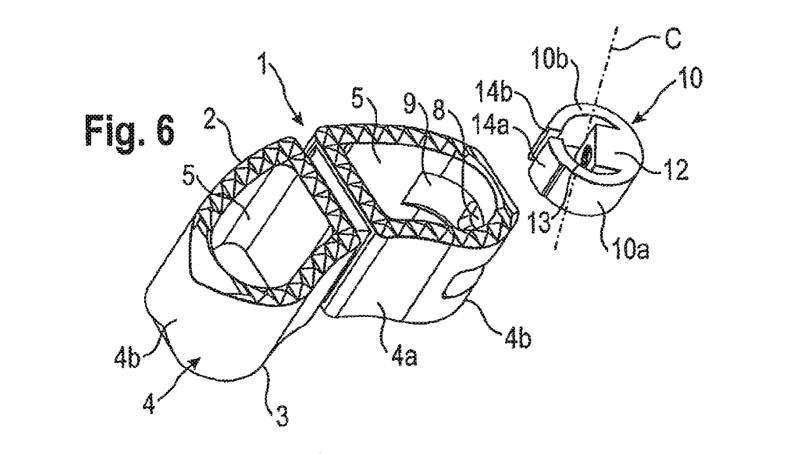
FIG. 6 shows a perspective view of the intervertebral implant of FIG. 1 before inserting the insert.
Figure 7:
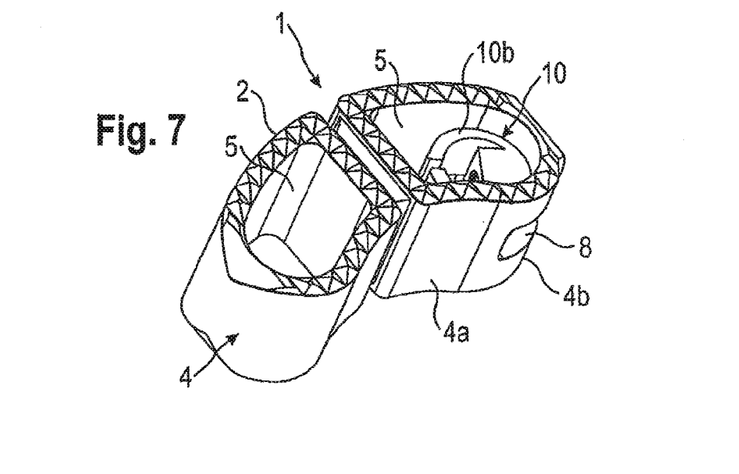
FIG. 7 shows a perspective view of the intervertebral implant of FIG. 6 with the insert mounted.

As shown in FIG. 6, a guide groove 9 is provided at the inner wall of the side wall 4 around the elongate opening 8. The guide groove 9 extends from both ends of the elongate opening into each of the long sides 4a of the side wall. The height of the guide groove 9 in a vertical direction (i.e., in a direction from the bottom face 3 to the top face 2) is the same or greater than the height of the elongate opening 8 in the vertical direction. The length of the guide groove 9 in a circumferential direction is dimensioned such that an insert 10, shown in FIGS. 1 to 7, can be accommodated and guided in the groove. When the insert 10 is inserted into the hollow interior section 5 and placed into the groove 9, the groove 9 prevents the insert 10 from falling out.

The insert 10 of the implant 1 according to the first embodiment is a substantially hollow cylindrical member. A cylinder axis C defines an axis of rotation. A slot 11 extends parallel to the cylinder axis C through the wall of the hollow cylinder to provide first and second flexible substantially semi-spherical arms 10a, 10b that can be compressed slightly towards each other, thereby narrowing the slot 11. At a position opposite to the slot 11, the insert 10 includes a solid portion 12, for example, a cuboid-like portion extending between the flexible arms 10a, 10b. The size of the solid portion 12 is such that it does not restrict the flexibility of the arms 10a, 10b. The solid portion 12 has a recess 13 for engagement with a tool 50. The recess 13 can be, for example, a threaded bore.

Figures 8A, 8B:
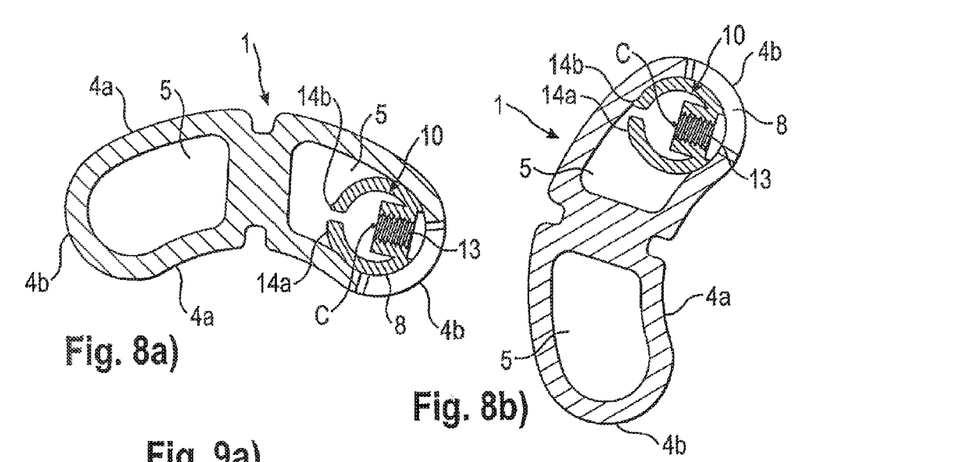
FIG. 8a shows a cross-sectional view of the intervertebral implant with the insert in a first position limited by a first stop.
FIG. 8b shows a cross-sectional view of the intervertebral implant with the insert in a second position limited by a second stop.

The first flexible arm 10a has at its outer wall, adjacent to its free end, a first stop in the form of a first protrusion 14a. The second flexible arm 10l) has at its outer wall, adjacent to its free end, a second stop in the form of a second protrusion 14b. As shown in FIGS. 8a and 8b, the insert 10 provides, with its cylinder axis C, an axis of rotation for the implant. Hence, when the insert 10 is inserted, it can be rotated relative to the rest of the implant between a first position defined by or limited by an abutment of the first protrusion 14a at the inner wall (FIG. 8a), and a second position defined by or limited by an abutment of the second protrusion 14b at the inner wall (FIG. 8b). The first protrusion 14a provides an abutment surface at a position away from the slot 11, such that when the insert 10 is within the guide groove 9 and the first protrusion 14a abuts against the inner wall of the side wall 4 of the implant, recess 13 is located at or opens near an end of the opening 8 opposite to where the first protrusion 14a is positioned. The second protrusion 14b is at a position at the free end of the second flexible arm 10l), such that the recess 13 is at the other end of the elongate opening 8 when the protrusion 14b abuts against the inner wall of the side wall 4 of the implant 1.

The tool 50 will now be explained with reference to FIGS. 1 to 9. The tool 50 includes a handle 51 that is connected to a drive shaft 52 (See, e.g., FIG. 9a) with an end portion 53 for engagement with the recess 13 of the insert 10. In the embodiment shown, the end portion 53 is a threaded end portion that engages a threaded bore of recess 13. The drive shaft 52 is rotatable within a sleeve 54 that is connected to a counter holding portion 55. An end portion 56 of the sleeve is concavely curved with a curvature that may be adapted to a curvature of the outer wall of the short side 4b of the side wall 4. The tool 50 is, however, not limited to the specific example shown, and may have various different constructions.

Figure 9A:
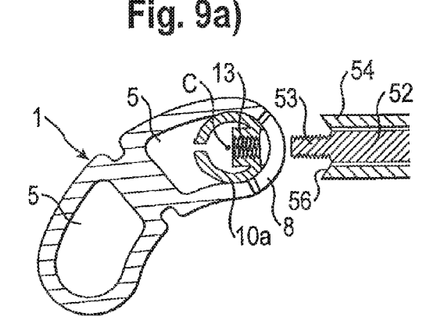
FIGS. 9a to 9d show schematic cross-sectional views of steps of engaging a tool with the intervertebral implant and rotating the implant according to an embodiment of the invention.
Figure 9B:
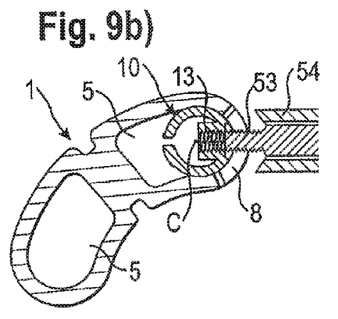
Figure 9C:
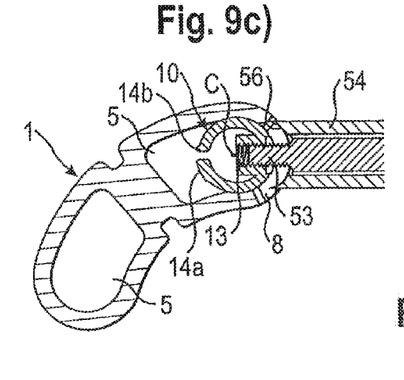
Figure 9D:
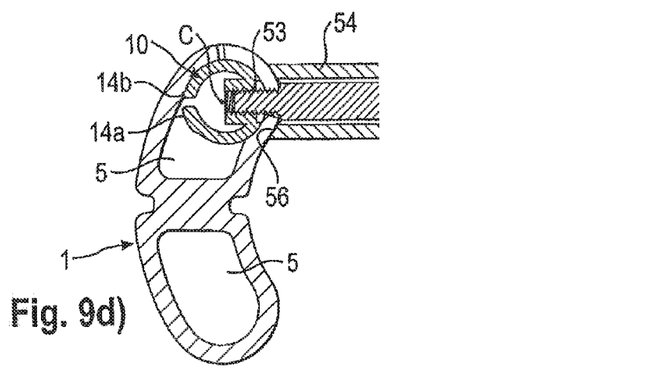

The connection between the tool and the implant will now be explained with reference to FIGS. 9a to 9d. When the insert 10 is inserted into the implant as shown in FIG. 9a, the recess 13 faces the opening 8. The recess 13 may then be engaged with the end portion 53 of the drive shaft 52. In the case of a threaded bore of recess 13 and a threaded end portion 53, screwing the end portion 53 into the bore results in clamping the short side 4b of the implant between the insert 10 and the end portion 56 of the sleeve 54 of the tool 50. The connection between the implant 1 and the tool 50 may be fixed in this configuration. A slight loosening of the threaded connection may allow for rotation of the insert 10 with tool 50 relative to the rest of the implant 1. The rotation is limited in both directions by the abutment surfaces of the protrusions 14a, 14b, respectively, at or against the side wall 4.

The implant 1, including the insert 10, is made of a biocompatible material. For example, the implant can be made of stainless steel or titanium, or of a biocompatible metal alloy, such as a nickel titanium alloy, for example Nitinol, or can be made of a biocompatible plastic material, for example, PEEK (polyetheretherketone).

Figure 10A:
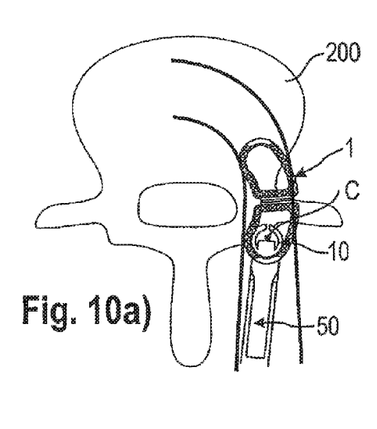
FIGS. 10a to 10f schematically show steps of inserting and positioning the intervertebral implant between two vertebral bodies according to an embodiment of the invention.

Use of the implant 1 during surgery will now be described with reference to FIGS. 10a to 10f. FIGS. 10a to 10f schematically show steps for inserting and positioning the intervertebral implant 1 into a space between two vertebral bodies of adjacent vertebrae 200. First, the tool 50 is connected to the implant 1. The insert 10 is in a position such that the recess 13 is positioned at approximately a center of the elongate opening 8 along a lengthwise direction of the opening 8. By tightening the connection between the insert 10 and the tool 50, the implant 1 is fixed to the tool 50. Then, as shown in FIG. 10a, the implant 1 is introduced into the intervertebral space between two neighboring vertebrae, where one of the vertebrae is shown as vertebra 200 in the drawings. The narrow side 4b of the implant 1 that is on a side of the implant 1 opposite to the tool 50 acts as a leading side. In the method shown, the intervertebral implant 1 is introduced into the space between the vertebral bodies using a posterior and lateral approach to access the space between the vertebral bodies.

Figure 10B:
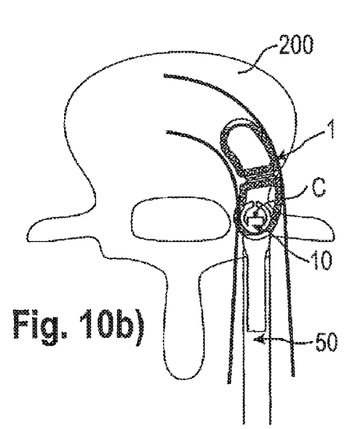
Figure 10C:
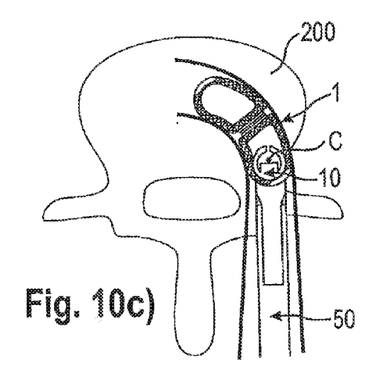
Figure 10D:
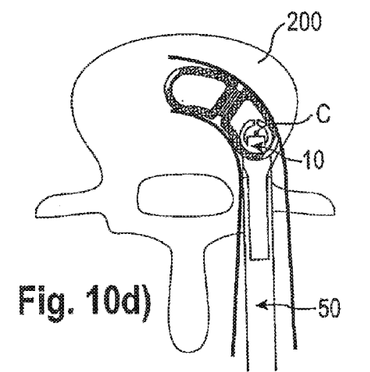
Figure 10E:
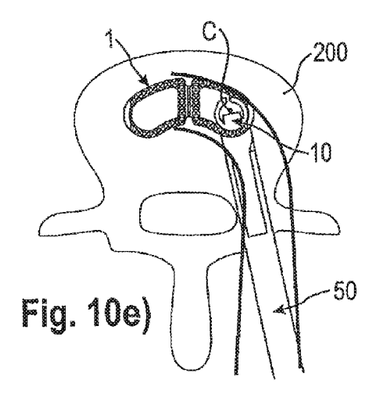
Figure 10F:
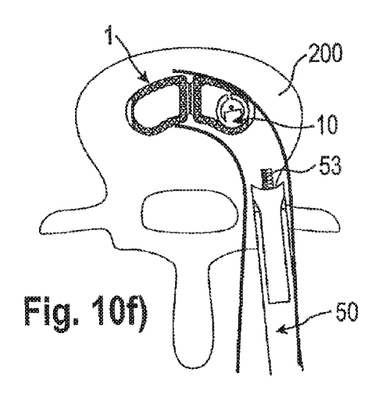

When the implant 1 and the tool 50 experience resistance and cannot be pushed or advanced further, as shown in FIG. 10b, the fixation between the implant 1 and the tool 50 is loosened slightly by screwing back the drive shaft 52 (e.g., by rotation). This loosens the clamping between the implant 1 and the tool 50 so that the implant 1 is rotatable about the cylinder axis C of the insert 10. As shown in FIGS. 10c and 10d, the implant 1 rotates around the cylinder axis C of the insert 10 so that the recess 13 of the insert 10 is shifted along the elongate opening 8. Then, as shown in FIG. 10e, the implant 1 is shifted to its final position. As depicted in FIG. 10f, thereafter, the tool 50 is disconnected by unscrewing the drive shaft 52 from the threaded recess 13 and is removed.

Since the tool 50 can be easily connected to and separated from the implant 1, the handling of the implant 1 is simplified. Meanwhile, during implantation, the implant 1 is safely connected to the tool 50 and cannot escape.

Furthermore, the design of the insert 10 is such that most of the hollow interior space remains available for fusion. The insert 10 remains with the implant 1 after implantation, and occupies very little space therein. As shown, for example in FIGS. 2 and 8a to 9d, when the insert 10 is positioned inside the hollow interior section 5 in position to be removably connected with the tool 50, there is more hollow space outside an outer surface of the insert 10 facing away from a center of the insert 10 than there is hollow space between the flexible arms 10a, 10b of the insert 10.

Figure 11:
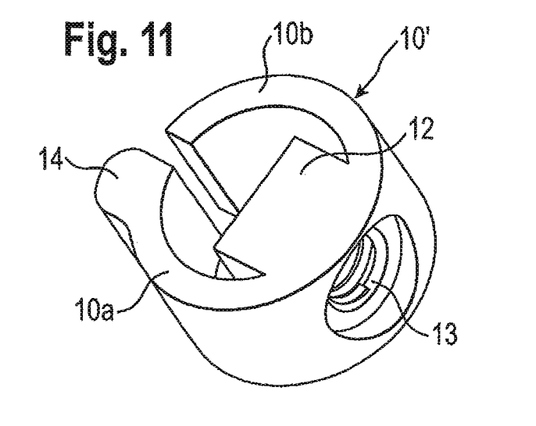
FIG. 11 shows a perspective top view of an insert according to a second embodiment of the intervertebral implant.
Figure 12:
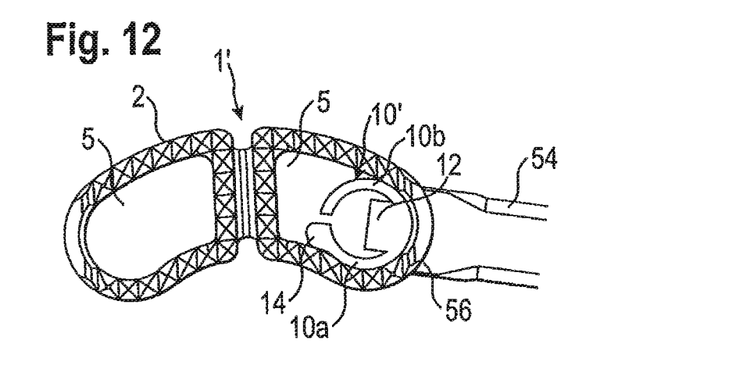
FIG. 12 shows a top view of the intervertebral implant according to the second embodiment with a tool connected to the intervertebral implant in a first position.
Figure 13:
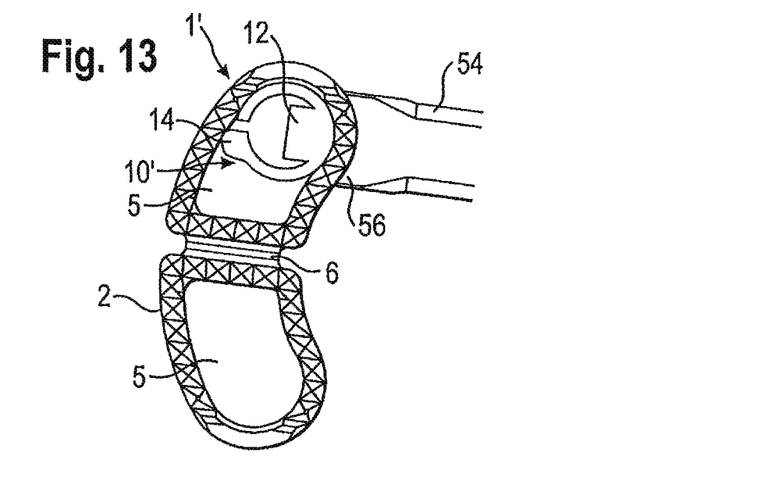
FIG. 13 shows a top view of the intervertebral implant according to the second embodiment with the tool connected thereto in a second position.

FIGS. 11 to 13 illustrate a second embodiment of the implant. The implant 1' differs from the implant 1 of the first embodiment in the designs of the inserts. The insert 10' of the second embodiment differs from the insert 10 of the first embodiment in the construction of the stops. All other parts of the implant 1' and the insert 10' are the same as in the first embodiment. The description thereof will not be repeated. The insert 10' has, instead of two separate stops provided at the flexible arms 10a, 10b, respectively, only one single protrusion 14 that is formed by a thickened end portion of the first flexible arm 10a. The thickened end portion 14 extends along the axial length of the insert 10' and is provided adjacent to the slot 11. By the thickened end portion 14, an outer diameter at the end of the flexible arm 10a is greater than an outer diameter at the flexible arm 10b. The size of the thickened end portion 14 is such that it can limit the rotation of the implant 10' between two positions, as shown in FIGS. 12 and 13. When the insert 10' is in a first position, the recess 13 of the insert 10' is positioned approximately at a center of the elongate opening 8 along a lengthwise direction of the opening 8. The thickened portion 14 abuts against one of the long sides 4a of the side wall 4. Here, the connection between the tool 50 and the implant 1' is substantially straight as shown in FIG. 12. When the insert 10' is rotated relative to the implant 1' by approximately 90', the thickened end portion 14 abuts against the opposite long side 4a of the side wall 4, and the recess 13 of the insert 10' is positioned at an end of the elongate opening 8 opposite to where the thickened portion 14 is positioned. The connection between the tool 50 and the implant 1' is substantially perpendicular, as shown in FIG. 13.

Figure 14:
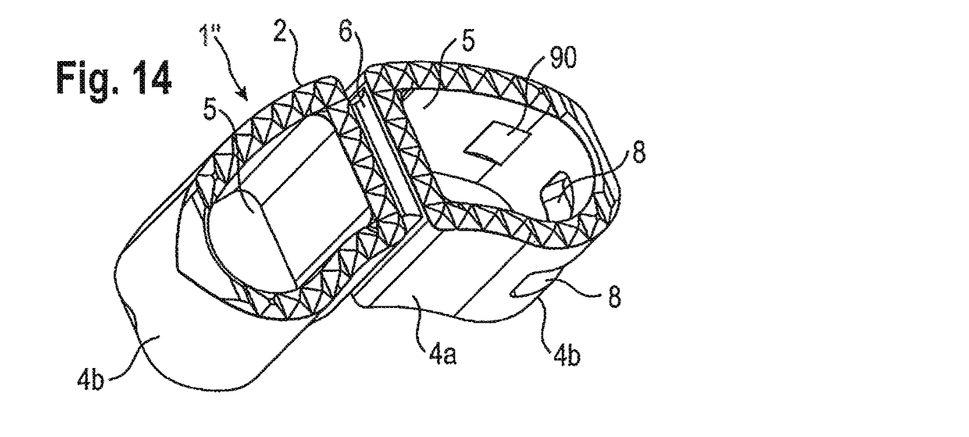
FIG. 14 shows a perspective top view of an intervertebral implant according to a third embodiment, where an insert is not yet mounted.
Figure 15:
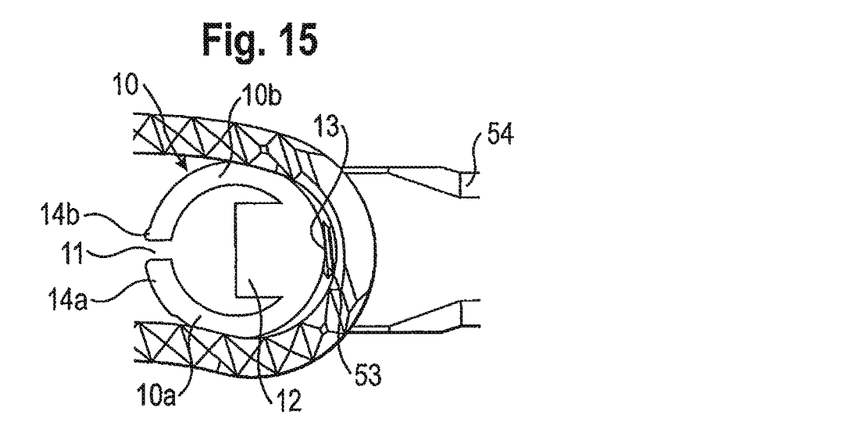
FIG. 15 shows a top view of the intervertebral implant of FIG. 14 according to the third embodiment, with an insert mounted and a tool connected to the intervertebral implant in a first position.
Figure 16:
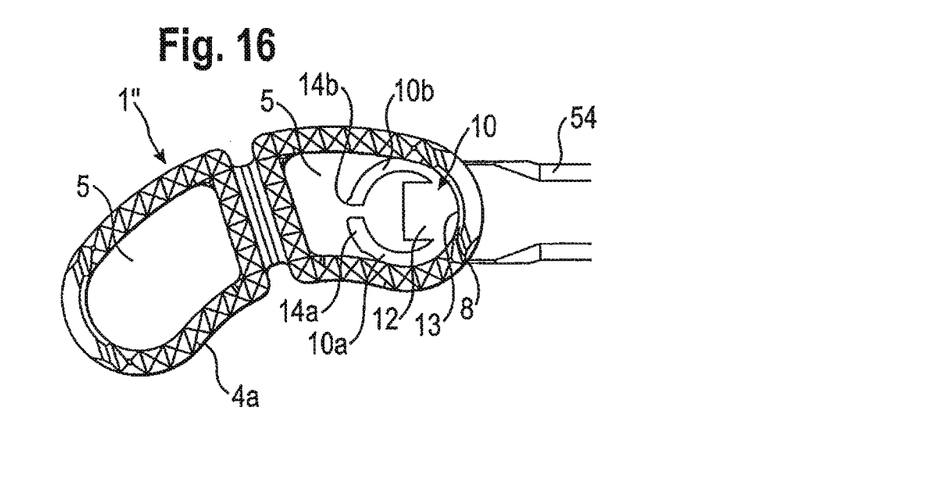
FIG. 16 shows the intervertebral implant with the tool according to the third embodiment in a second position.
Figure 17:
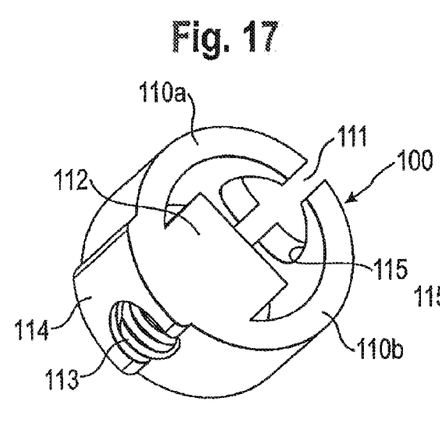
FIG. 17 shows a perspective top view of an insert of an intervertebral implant according to a fourth embodiment.
Figure 18:
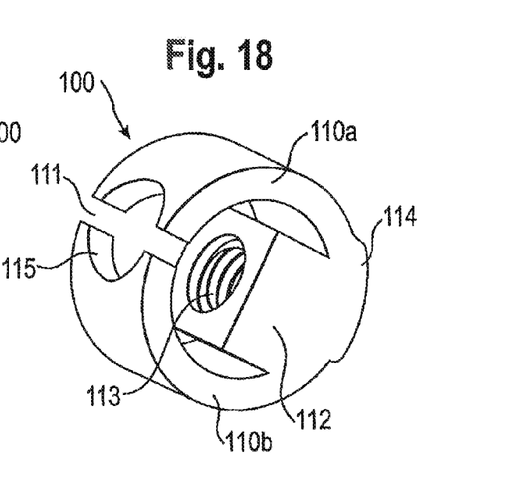
FIG. 18 shows a perspective bottom view of the insert of the intervertebral implant according to the fourth embodiment.

A third embodiment of the implant is illustrated in FIGS. 14 to 16. The implant 1" differs from the implant 1 according to the first embodiment by the positions of the guide grooves. The guide groove 90 includes two groove parts located opposite to each other at the inner wall of the side wall 4, in the areas of the long sides 4a. The groove parts of the guide groove 90 are located at a distance from the elongate opening 8. When the insert 10 is inserted into the hollow interior section 5, a portion of each of the flexible arms 10a, 10b is received in the guide groove 90, respectively. As can be seen in FIG. 15, in some embodiments, the position of the guide groove 90 is such that when the insert 10 is inserted, there is a distance between the recess 13 and the opening 8.

FIG. 15 shows the engagement of the end portion 53 of the drive shaft 52 of the tool 50 with the recess 13 of the insert 10. Since there is a distance between the insert 10 and the opening 8, the connection is not fixed and the rest of the implant 1" can be rotated around the insert 10. By further engagement of the tool 50 and the insert 10, the insert is drawn against the opening 8 by slightly compressing the flexible arms 10a, 10b, so that the connection between the implant 1" and the tool can be fixed.

The implant 1" can also be equipped with the insert 10' according to FIGS. 11 to 13.

A fourth embodiment of the implant is shown in FIGS. 17 to 20. The implant according to the fourth embodiment includes an insert 100 that is different from the inserts 10 and 10' of the previous embodiments in that the insert 100 can be mounted such that the flexible portions 110a, 110b of the insert 100 are facing towards the elongate opening 8. The insert 100 is a substantially hollow cylindrical part, similarly as seen in the previous embodiments, and has a slot 111 forming two flexible arms 110a, 110b. Opposite to the slot 111, a solid portion 112 extends into the space between the flexible arms 110a, 110b. The solid portion 112 has an engagement portion 113 for the tool 50, which can be a threaded through hole. At an outer side of the insert 100 that faces away from the slot 111, the insert 100 includes a protrusion 114 that, in some embodiments, extends from the threaded through hole 113 asymmetrically toward a side of the first flexible arm 110a. The protrusion 114 acts as a stop to limit rotation of the insert 100 relative to the rest of the implant 1'" in two directions. The insert 100 further has a circular recess 115 that is provided at the position of the slot 111 to allow the end portion 53 of the tool 50 to be guided therethrough.

Figure 19:
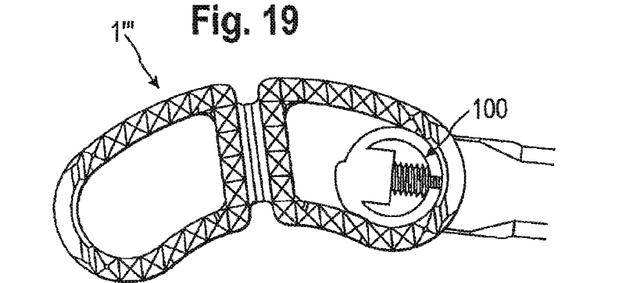
FIG. 19 shows a top view of the intervertebral implant with insert according to the fourth embodiment and a tool connected thereto in a first position.
Figure 20:
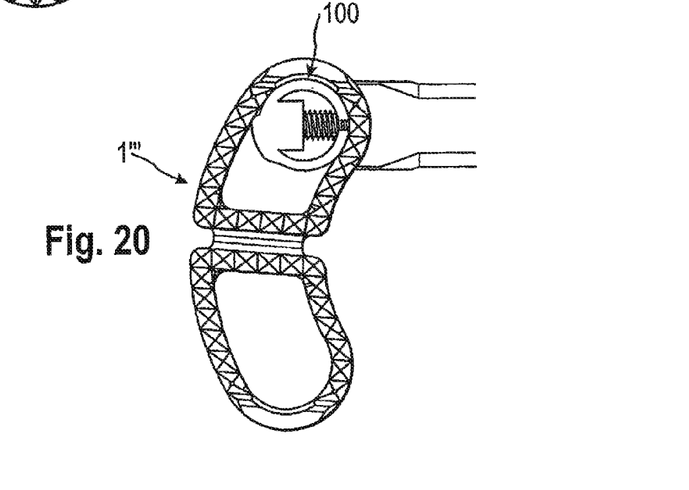
FIG. 20 shows a top view of the intervertebral implant with the tool according to the fourth embodiment in a second position.
Figure 21:
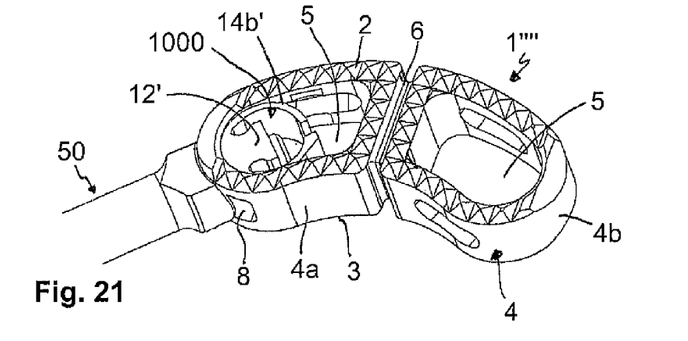
FIG. 21 shows a perspective view from a top of an intervertebral implant with insert according to a fifth embodiment, and the tool connected thereto in a first position.
Figure 22:
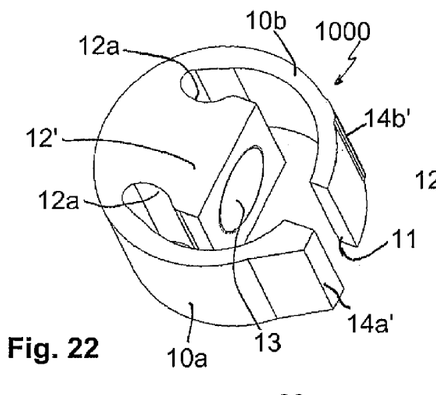
FIG. 22 shows a perspective view of an insert corresponding to the intervertebral implant according to the fifth embodiment.
Figure 23:
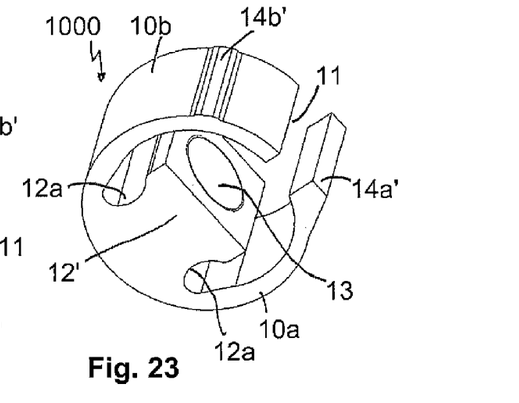
FIG. 23 shows another perspective view of the insert corresponding to the intervertebral implant according to the fifth embodiment.
Figure 24:
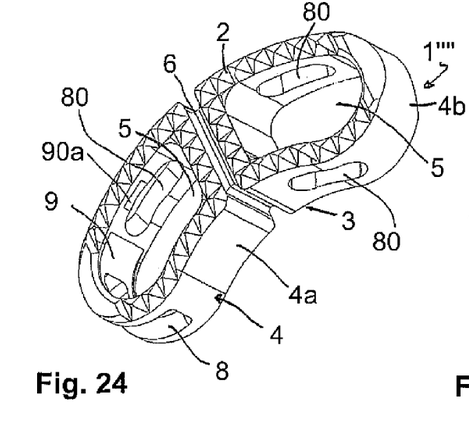
FIG. 24 shows a perspective view of the intervertebral implant without the insert according to the fifth embodiment.
Figure 25:
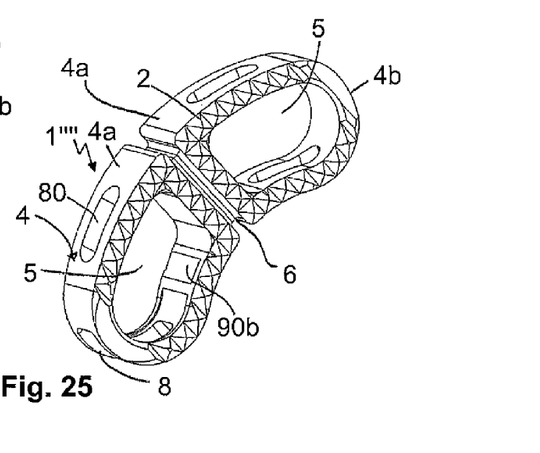
FIG. 25 shows another perspective view of the intervertebral implant without the insert according to the fifth embodiment.

FIGS. 19 and 20 show a top view of the implant 1'" with the insert 100 mounted therein. The insert 100 is mounted such that the flexible arms 110a, 110b are oriented towards the opening 8. Hence, the threaded through hole 113 is positioned at a distance from the opening 8. The end portion 53 of the drive shaft 52 of the tool 50 is guided through the elongate opening 8 and engages the threaded through hole 113. A size of the circular recess 115 is such that the end portion 53 can pass therethrough. When a threaded connection between the end portion 53 and the through hole 113 is tightened, the flexible arms 110a, 110b are slightly compressed and drawn against the opening 8 and/or the inner wall of the side wall 4. Thereby, the connection between the implant 1''' and the tool 50 can be fixed. Loosening the connection allows a rotation of the implant 1''' relative to the tool 50. As shown in FIG. 19, the movement of the implant 1''' relative to the tool 50 is limited in a first direction when the protrusion 114 abuts against one of the long sides 4a of the side wall 4. In this position, the threaded through hole 113 points to approximately a center of the elongate opening 8. When the implant 1''' is rotated with respect to the tool 50, the other or opposite portion of the protrusion 114 abuts against the other or opposite one of the long sides 4a of the side wall 4, to limit the rotational motion in the second direction. The range of motion is around 90°.

A fifth embodiment of the implant is shown in FIGS. 21 to 25. Parts and portions that are identical or similar to the previous embodiments are indicated with the same reference numerals, and the descriptions thereof are therefore not repeated. In this embodiment, a protrusion 1413' on insert 1000 is positioned on arm 10b at a position away from slot 11 in a circumferential direction. A position of the protrusion 14b' is selected such that when the insert 1000 is rotated relative to the implant into an end position similar to that shown in FIG. 8b, the protrusion 14b' snaps into groove 9. This may give feedback to a surgeon or other practitioner that such an end position has been reached.

Furthermore, side walls of solid portion 12' that face inner walls of flexible arms 10a, 10b each have a curved recess 12a to facilitate insertion of the insert 1000 between inner walls of implant 1''''.

The implant 1'''' may further have elongate openings 80 in sidewall 4 and additional grooves 90a, 90b. In particular, on a long side 4a, there may be additional elongate openings 80, for example, to allow ingrowth of bone material and vessels. Meanwhile, the grooves 90a, 90b at the long sides 4a may serve for easier insertion of the insert 1000 into interior hollow section 5. In such embodiments, once the insert 1000 has been inserted into the interior hollow section 5 at the position of the grooves 90a, 90b, the insert 1000 may then be displaced relative to the rest of the implant 1'''' into the groove 9.

Various modifications of the embodiments are also possible. The contour and the shape of the implant may be different from the examples shown. For example, the contour may have any other shape, such as circular, rectangular, oval, etc. A height of the side wall 4 may be constant throughout the implant. The center wall 6 can be omitted. It is also possible to adapt existing intervertebral implants that may not include such an opening, by providing the implants with an elongate opening, a guide groove, and an insert piece as described above.

The insert also does not have to include stops. When the tool 50 is connected to the implant, an abutment of the end portion 53 of the tool 50 at the ends of the elongate opening 8 may also provide for limiting the relative movement between the pieces. However, the stops may be useful to limit the motion of the insert once it is inserted into the implant when the tool is not yet connected. The constructions of the various embodiments may also be interchangeable. For example, it is possible to have a design with the two groove portions 90 in any of the embodiments shown. The positions and shapes of the protrusions that act as stops can also vary. In particular, the shapes can be different. The elongate opening 8 can be provided at another position and/or several openings can be provided.

In addition, the connection between the insert and the tool need not be a threaded connection. Any other connection that can be easily fixed and loosened, for example, a snap-in connection, may also be utilized.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An intervertebral implant comprising:
a first surface configured to engage a first vertebral body;
a second surface configured to engage a second vertebral body;
a side wall connecting the first surface and the second surface along an axial direction of the side wall and an inner wall surface of the side wall defining a hollow space of the implant;
a guide groove into the inner wall surface of the side wall; and
a rotatable insert configured to be positioned into the guide groove from the hollow space;
wherein an elongate opening extends through the side wall into the hollow space and has a maximum length in a circumferential direction of the side wall that is greater than a maximum length of the opening in the axial direction of the side wall;
wherein the insert comprises an engagement portion and a spring portion, the engagement portion having a connection feature configured to be removably connected with a tool through the opening when the insert is positioned in the guide groove such that the insert is configured to remain implanted by disconnecting the tool;
wherein the spring portion comprises a flexible arm extending from the engagement portion, the flexible arm being compressible toward the engagement portion to position the insert in the guide groove; and
wherein when the insert is positioned in the guide groove, the connection feature of the insert is rotatable from a location adjacent one circumferential end of the elongate opening to a location adjacent a second circumferential end of the elongate opening.

2. The intervertebral implant of claim 1, wherein the guide groove comprises two opposing guide grooves into the inner wall surface of the side wall and each guide groove opens into the hollow space and wherein the spring portion comprises two flexible arms being compressible toward the engagement portion to position the insert in the guide grooves.

3. The intervertebral implant of claim 1, wherein the insert provides an axis of rotation for the intervertebral implant, the axis of rotation extending through an opening of the first surface into the space and through an opening of the second surface into the space when the insert is positioned in the space.

4. The intervertebral implant of claim 1, wherein the insert is configured to be guided in the guide groove during rotation of the insert.

5. The intervertebral implant of claim 4, wherein the guide groove is directly adjacent the opening of the implant.

6. The intervertebral implant of claim 4, wherein the guide groove comprises two opposing guide grooves into the inner wall surface of the side wall and each guide groove opens into the hollow space.

7. The intervertebral implant of claim 1, wherein the insert comprises a substantially cylindrical wall, and has a slot extending through the wall in an axial direction of the insert.

8. The intervertebral implant of claim 7, wherein the engagement portion includes an opening to the connection feature for the tool, and wherein when the insert is positioned inside the hollow space in position to be removably connected with the tool, the opening of the engagement portion is between the slot of the insert and the elongate opening.

9. The intervertebral implant of claim 7, wherein the engagement portion includes an opening to the connection feature for the tool, and wherein when the insert is positioned inside the hollow space in position to be removably connected with the tool, the slot of the insert is between the opening of the engagement portion and the elongate opening.

10. The intervertebral implant of claim 1, wherein at least one stop is provided that limits rotation of the insert when the insert is positioned in the space.

11. The intervertebral implant of claim 10, wherein a slot extends along an outer wall of the insert into the space in an axial direction of the insert, and wherein the at least one stop is on the insert and is spaced apart from the slot of the outer wall of the insert.

12. The intervertebral implant of claim 1, wherein the side wall defines a height of the implant, and wherein a height of the insert is less than the height of the implant.

13. The intervertebral implant of claim 1, wherein the side wall has a first curvature along the elongate opening, and wherein the insert has an outer wall with a curvature corresponding to the first curvature.

14. The intervertebral implant of claim 1, wherein at least a second elongate opening extends through the side wall into the space.

15. The intervertebral implant of claim 1, wherein when the insert is positioned in the guide groove, the insert is rotatable by around 90° in the circumferential direction of the side wall.

16. The intervertebral implant of claim 15, wherein the insert comprises at least one stop that limits rotation of the insert when the insert is positioned in the guide groove.

17. An intervertebral implant comprising:
a first surface configured to engage a first vertebral body;
a second surface configured to engage a second vertebral body;
a side wall connecting the first surface and the second surface and defining a hollow space of the implant; and
a rotatable insert configured to be positioned in the hollow space;
wherein an elongate opening extends through the side wall into the space;
wherein the insert comprises an engagement portion and a spring portion, the engagement portion having a connection feature configured to be removably connected with a tool through the opening when the insert is positioned in the space such that the insert is configured to remain implanted by disconnecting the tool;
wherein the spring portion comprises a flexible arm extending from the engagement portion, the flexible arm being compressible toward the engagement portion to hold the insert in the space by frictional engagement with the side wall;
wherein at least one stop is provided that limits rotation of the insert when the insert is positioned in the space; and
wherein the at least one stop limits the rotation of the insert relative to other portions of the implant to around 90°.

18. A method of inserting an implant into a space between two vertebral bodies, the implant comprising a first surface configured to engage a first vertebral body, a second surface configured to engage a second vertebral body, a side wall connecting the first surface and the second surface and defining a hollow space of the implant, and a rotatable insert configured to be positioned in the hollow space of the implant, wherein an elongate opening extends through the side wall into the space, and wherein the insert comprises an engagement portion and a spring portion, the engagement portion having a connection feature configured to be removably connected with a tool through the opening when the insert is positioned in the space such that the insert is configured to remain implanted by disconnecting the tool, and wherein the spring portion comprises a flexible arm extending from the engagement portion, the flexible arm being compressible toward the engagement portion to hold the insert in the space by frictional engagement with the side wall, the method comprising:
connecting a tool to the engagement portion of the insert through the opening, such that a rotational orientation of the implant relative to the tool is fixed;
inserting the implant into a space between two vertebral bodies to a first position;
loosening the connection between the tool and the implant, such that the rotational orientation of the implant relative to the tool is adjustable;
further inserting the implant into the space between the two vertebral bodies to a second position, wherein the rotational orientation of the implant relative to the tool changes between the first and second positions; and
disconnecting the tool from the implant with the insert remaining implanted.

19. The method of claim 18, further comprising inserting and positioning the insert in the space of the implant prior to connecting the tool to the implant.

20. The method of claim 18, wherein when the rotational orientation of the implant relative to the tool changes, a rotational orientation of the insert relative to the tool remains fixed.

21. The method of claim 20, wherein the implant rotates relative to a central axis of the insert with an axis of rotation extending through an opening of the first surface into the hollow space and through an opening of the second surface into the hollow space when the insert is positioned in the hollow space of the implant.

22. The method of claim 18, wherein the tool and the engagement portion of the insert form a threaded connection to facilitate the connecting, loosening, and disconnecting between the tool and the implant.

23. An intervertebral implant comprising:
a first surface configured to engage a first vertebral body;
a second surface configured to engage a second vertebral body;
a side wall connecting the first surface and the second surface and defining interior hollow space of the implant between the first surface and the second surface such that the interior hollow space extends through the first surface and the second surface; and
a rotatable insert configured to be positioned in the interior hollow space, the insert being configured to be significantly smaller than the interior hollow space such that most of the interior hollow space is unoccupied by the insert;

wherein an elongate opening extends through the side wall of the implant into the space;

wherein the insert comprises an engagement portion and a spring portion, the engagement portion having a connection feature configured to be removably connected with a tool through the opening when the insert is positioned in the space such that the insert is configured to remain implanted by disconnecting the tool, the insert comprising an upper surface, a lower surface, a side wall connecting the upper surface and the lower surface, and an outer surface of the side wall of the insert facing away from a center of the insert;

wherein the spring portion comprises two flexible arms extending from the engagement portion, the flexible arms being compressible toward the engagement portion to hold the insert in the space by frictional engagement with the side wall of the implant; and wherein when the insert is positioned inside the interior hollow space in position to be removably connected with the tool, and when viewing a cross-section of the implant from the upper surface of the insert, there is more hollow space outside the outer surface of the insert than there is hollow space between the flexible arms of the insert.

* * * * *

UNITED STATES PATENT AND TRADEMARK OFFICE
CERTIFICATE OF CORRECTION

PATENT NO. : 9,492,286 B2  
APPLICATION NO. : 13/494871  
DATED : November 15, 2016  
INVENTOR(S) : Lutz Biedermann et al.

Page 1 of 1

It is certified that error appears in the above-identified patent and that said Letters Patent is hereby corrected as shown below:

In the Specification

Column 4, Line 15     Delete "arm 101)",  
                            Insert --arm 10*b*--

Column 4, Line 32     Delete "arm 101),",  
                            Insert --arm 10*b*,--

Column 6, Line 39     Delete "implant according",  
                            Insert --implant 1'" according--

Column 7, Line 23     Delete "protrusion 1413'",  
                            Insert --protrusion 14*b*'--

Signed and Sealed this  
First Day of May, 2018

Andrei Iancu  
*Director of the United States Patent and Trademark Office*